US00PP34489P2

(12) United States Plant Patent
Boynton-Steele

(10) Patent No.: US PP34,489 P2
(45) Date of Patent: Aug. 9, 2022

(54) ***SALVIA* PLANT NAMED 'MSWNBOYTON1'**

(50) Latin Name: ***Salvia mohavensis* x *Salvia clevelandii***
Varietal Denomination: 'MSWNBoyton1'

(71) Applicant: Nich Boynton-Steele, Boise, ID (US)

(72) Inventor: Nich Boynton-Steele, Boise, ID (US)

( * ) Notice: Subject to any disclaimer, the term of this patent is extended or adjusted under 35 U.S.C. 154(b) by 0 days.

(21) Appl. No.: 17/543,632

(22) Filed: Dec. 6, 2021

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Salvia* plant named 'MSWNBoyton1', characterized by its relatively compact, upright and outwardly spreading plant habit; freely branching habit and vigorous growth habit; bushy appearance; greyish olive green-colored leaves; relatively large inflorescences with pale blue-colored flowers; long flowering period; and relative tolerance to high temperatures and dry or wet conditions.

2 Drawing Sheets

Figure 1:
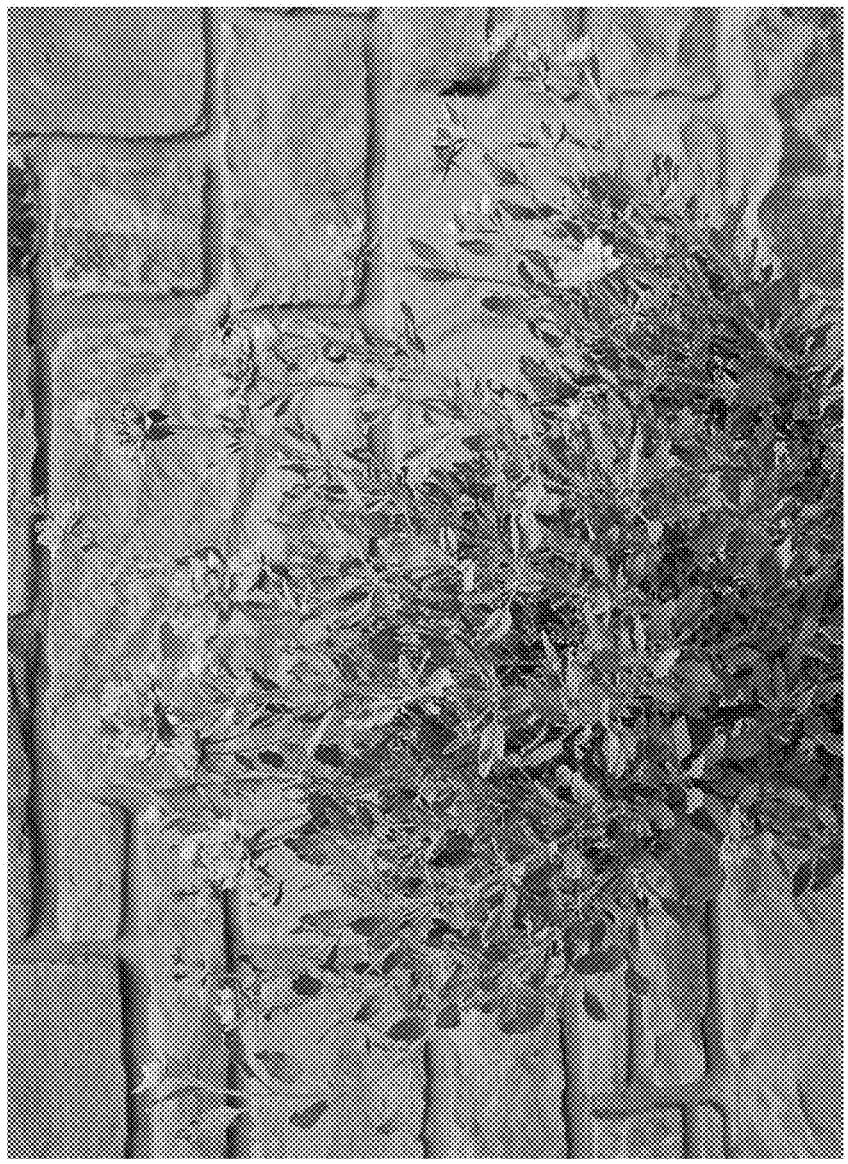

Botanical designation: *Salvia mohavensis* x *Salvia clevelandii.*

Cultivar denomination: 'MSWNBoyton1'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Salvia* plant, botanically known as *Salvia mohavensis* x *Salvia clevelandii* and hereinafter referred to by the name 'MSWNBoyton1'.

The new *Salvia* plant is a product of a planned breeding program conducted by the Inventor in Tucson, Ariz. The objective of the breeding program is to create new long-lived *Salvia* plants with high temperature tolerance, tolerance to dry and wet conditions and long flowering season.

The new *Salvia* plant originated from a cross-pollination conducted by the Inventor in May, 2012 of an unnamed selection of *Salvia mohavensis*, not patented, as the female, or seed, parent with an unnamed selection of *Salvia clevelandii*, not patented, as the male, or pollen, parent. The new *Salvia* plant was discovered and selected by the Inventor as a single flowering plant from within the progeny of the stated cross-pollination grown in a controlled environment in Tucson, Ariz. in May, 2013.

Asexual reproduction of the new *Salvia* plant by softwood vegetative cuttings in Tucson, Ariz. since May, 2017, has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'MSWNBoyton1'. These characteristics in combination distinguish 'MSWNBoyton1' as a new and distinct cultivar of *Salvia:*

1. Relatively compact, upright and outwardly spreading plant habit.
2. Freely branching habit and vigorous growth habit; bushy appearance.
3. Greyish olive green-colored leaves.
4. Relatively large inflorescences with pale blue-colored flowers.
5. Long flowering period.
6. Relatively tolerant to high temperatures and dry or wet conditions.

Plants of the new *Salvia* can be compared to plants of the female parent selection. Plants of the new *Salvia* differ from plants of the female parent selection in the following characteristics:

1. Plants of the new *Salvia* have shorter internodes and are denser than plants of the female parent selection.
2. Plants of the new *Salvia* have larger inflorescences than plants of the female parent selection.
3. Plants of the new *Salvia* are more tolerant to low temperature and wet conditions than plants of the female parent selection.

Plants of the new *Salvia* can be compared to plants of the male parent selection. Plants of the new *Salvia* differ from plants of the male parent selection in the following characteristics:

1. Plants of the new *Salvia* have larger inflorescences than plants of the male parent selection.
2. Flowers of plants of the new *Salvia* are lighter blue in color than flowers of plants of the male parent selection.
3. Plants of the new *Salvia* are more tolerant to low temperature and wet conditions than plants of the male parent selection.

Plants of the new *Salvia* can be compared to plants of an unnamed selection of *Salvia greggii* known to the Inventor, not patented. In side-by-side comparisons, plants of the new *Salvia* differed from plants of the unnamed selection of *Salvia greggii* in the following characteristics:

1. Plants of the new *Salvia* have greyish olive green-colored leaves whereas plants of the unnamed selection of *Salvia greggii* have green-colored leaves.
2. Plants of the new *Salvia* have larger inflorescences than plants of the unnamed selection of *Salvia greggii.*
3. Plants of the new *Salvia* have pale blue-colored flowers whereas plants of the unnamed selection of *Salvia greggii* have pinkish red-colored flowers.
4. Plants of the new *Salvia* are more tolerant to high temperatures than plants of the unnamed selection of *Salvia greggii.*

Plants of the new *Salvia* can also be compared to plants of an unnamed selection of *Salvia chamaedryiodes* known to the Inventor, not patented. In side-by-side comparisons, plants of the new *Salvia* differed from plants of the unnamed selection of *Salvia chamedryiodes* in the following characteristics:

1. Plants of the new *Salvia* are more upright than and not as low-growing as plans of the unnamed selection of *Salvia chamaedryiodes.*
2. Plants of the new *Salvia* have greyish olive green-colored leaves whereas plants of the unnamed selection of *Salvia chamaedryiodes* have silvery green-colored leaves.
3. Plants of the new *Salvia* have larger inflorescences than plants of the unnamed selection of *Salvia chamaedryiodes.*
4. Plants of the new *Salvia* are more tolerant to wet conditions than plants of the unnamed selection of *Salvia chamaedryiodes.*

BRIEF DESCRIPTION OF THE PHOTOGRAPHS

The accompanying colored photographs illustrate the overall appearance of the new *Salvia* plant, showing the colors as true as it is reasonably possible to obtain in colored reproductions of this type. Colors in the photographs may differ slightly from the color values cited in the detailed botanical description which accurately describe the actual colors of the new *Salvia* plant.

The photograph on the first sheet (FIG. 1) comprises a side perspective view of a typical flowering plant of 'MSWNBoyton1' grown in container.

Figure 2:
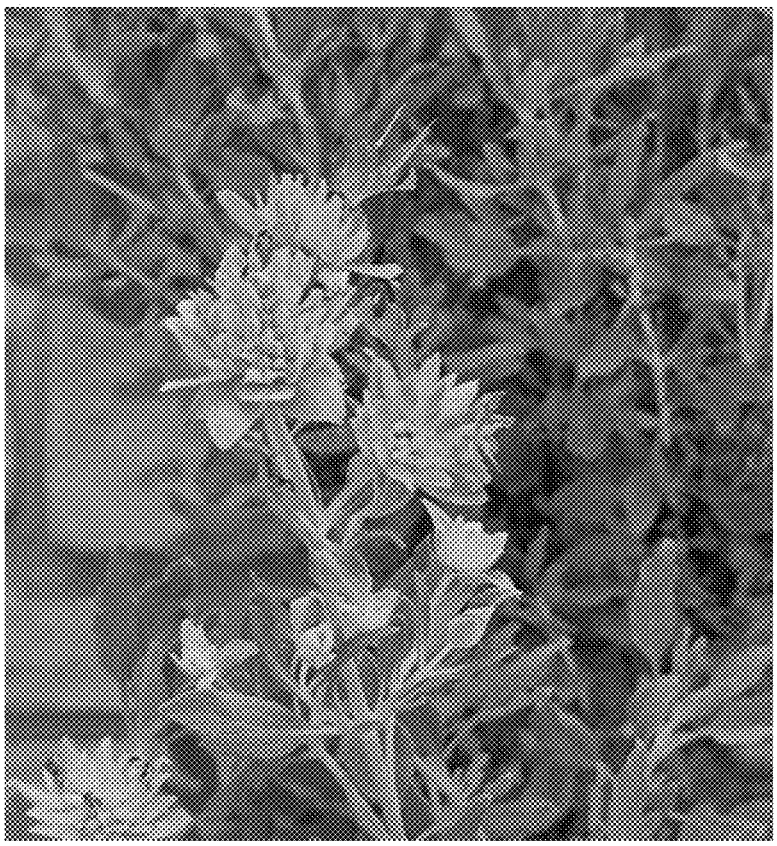

The photograph on the second sheet (FIG. 2) is a close-up view of a typical flowering plant of 'MSWNBoyton1'.

DETAILED BOTANICAL DESCRIPTION

The aforementioned photographs and following observations and measurements describe plants grown during the spring and summer in containers in outdoor nurseries in Glendale, Ariz. and Fort Worth, Tex. and under cultural practices typical of commercial *Salvia* production. Plants were three years old when the photographs and description were taken. During the production of the plants, day temperatures ranged from about 10° C. to 48° and night temperatures ranged from about 1° C. to 32°. In the following description, color references are made to The Royal Horticultural Society Colour Chart, 2015 Edition, except where general terms of ordinary dictionary significance are used.

Botanical classification: *Salvia mohavensis* X *Salvia clevelandii* 'MSWNBoyton1'.

Parentage:

*Female, or seed, parent.*—Unnamed selection of *Salvia mohavensis*, not patented.

*Male, or pollen, parent.*—Unnamed selection of *Salvia clevelandii*, not patented.

Propagation:

*Type.*—By softwood vegetative cuttings.

*Time to initiate roots, summer.*—About 15 days at soil temperatures about 27° C.

*Time to initiate roots, winter.*—About 21 days at soil temperatures about 22° C.

*Time to produce a rooted young plant, summer.*—About 60 days at soil temperatures about 27° C.

*Time to produce a rooted young plant, winter.*—About 100 days at soil temperatures about 22° C.

*Root description.*—Fine, fibrous; typically white to light brown in color, actual color of the roots is dependent on substrate composition, water quality, fertilizer type and formulation, substrate temperature and physiological age of roots.

*Rooting habit.*—Freely branching; dense.

Plant description:

*Type.*—Herbaceous perennial.

*Form.*—Upright and outwardly spreading plant form; broad inverted triangle; flowers arranged on upright terminal cymes.

*Branching habit.*—Freely basal branching with plants potentially developing lateral branches at every node.

*Growth habit.*—Vigorous.

*Plant height.*—About 38 cm.

*Plant width.*—About 73 cm.

*Lateral branch description.*—Length: About 28 cm. Diameter: About 2 mm. Internode length: About 2.2 cm. Strength: Strong, flexible. Aspect: Mostly upright; with subsequent development, decumbent. Texture: Densely covered with very fine pubescence. Color, developing: Close to 145B. Color, developed: Close to 178A to 178B.

Leaf description:

*Arrangement.*—Opposite, simple.

*Length.*—About 2.8 cm.

*Width.*—About 1.2 cm.

*Shape.*—Narrowly ovate.

*Apex.*—Broadly acute.

*Base.*—Cuneate.

*Margin.*—Crenate.

*Texture, upper and lower surfaces.*—Smooth, glabrous; slightly rugose.

*Fragrance.*—Strongly aromatic.

*Venation pattern.*—Pinnate.

*Color.*—Developing and fully expanded leaves, upper surface: Close to NN137B; venation, close to NN137B. Developing and fully expanded leaves, lower surface: Close to 146A; venation, close to 146B.

*Petiole length*.—About 1.5 cm.

*Petiole diameter*.—About 1 mm.

*Petiole texture, upper and lower surfaces*.—Smooth, glabrous.

*Petiole color, upper surface*.—Close to 143A.

*Petiole color, lower surface*.—Close to 146B.

Flower description:

*Flower arrangement and shape*.—Single bilabiate flowers arranged in terminal cymes; flowers face upright to outwardly depending on position in the inflorescence.

*Flowering habit*.—Freely flowering habit, numerous inflorescences each with about 25 to 30 flowers per inflorescence.

*Natural flowering season*.—Continuous flowering during the summer in the Southwestern United States; plants re-flower after removal of fully developed inflorescences.

*Flower longevity on the plant*.—About five to ten days; flowers not persistent.

*Fragrance*.—None detected.

*Flower buds*.—Length: About 5.5 mm. Diameter: About 3 mm. Shape: Ovoid. Color: Close to 144A.

*Inflorescence size*.—Length: About 2.25 cm. Diameter: About 2 cm.

*Flowers*.—Size: About 6 mm by 7 mm. Depth (height): About 1.1 cm.

*Petals*.—Arrangement: Two, fused at the base. Length, upper lip: About 1 cm. Length, lower lip: About 9 mm. Width, upper lip: About 5.5 mm. Width, lower lip: About 6 mm. Shape, upper lip: Broadly elliptic; apex, rounded; margin, entire. Shape, lower lip: Spatulate; apex, lobes obtuse; margin, entire. Texture and luster, upper and lower surfaces: Smooth, glabrous; matte. Color: Upper and lower lips, when opening and fully opened, upper surface: Close to 104B to 104C. Upper and lower lips, when opening and fully opened, lower surface: Close to 104B to 104C.

*Sepals*.—Arrangement: Five sepals fused into a tube. Length: About 7.5 mm. Width: About 1.5 mm. Shape: Narrowly deltoid. Apex: Acute. Margin: Entire. Texture and luster, upper and lower surfaces: Slightly pubescent; matte. Color, upper surface: Close to 145A. Color, lower surface: Close to 144A.

*Peduncles*.—Strength: Strong. Length: About 1.75 cm. Diameter: About 1 mm. Aspect: Erect to about 45° from vertical. Texture: Smooth, glabrous. Color: Close to 145A.

*Pedicels*.—Strength: Strong. Length: About 1 mm. Diameter: Less than 1 mm. Aspect: Erect to about 45° from vertical depending on position on the inflorescence. Texture: Smooth, glabrous. Color: Close to 145A.

*Reproductive organs*.—Stamens: Quantity per flower: Two; anthers dorsifixed. Filament length: About 0.1 mm. Filament color: Close to 157A. Anther shape: Oblong. Anther length: About 0.25 mm. Anther color: Close to 145A. Pollen amount: None observed. Pistils: Quantity per flower: One. Pistil length: About 7 mm. Stigma shape: Cleft, two-parted. Stigma color: Close to 154D. Style length: About 6 mm. Style color: Close to 154D. Ovary color: Close to 144A.

*Seeds and fruits*.—To date, seed and fruit production has not been observed on plants of the new *Salvia*.

Pathogen & pest resistance: To date, plants of the new *Salvia* have not been observed to be resistant to pathogens and pests common to *Salvia* plants.

Garden performance: Plants of the new *Salvia* have been observed to have good garden performance and to tolerate full sun condition, partial shade conditions, rain, wind, arid conditions and temperatures ranging from about −23° C. to 48° C.

It is claimed:

1. A new and distinct *Salvia* plant named 'MSWNBoyton1' as illustrated and described.

* * * * *